(12) United States Patent
Hayner et al.

(10) Patent No.: US 6,524,268 B2
(45) Date of Patent: Feb. 25, 2003

(54) COMBINATION URETERAL INFUSION CATHETER/DRAINAGE STENT

(76) Inventors: George M. Hayner, 408 Platt Ave., West Haven, CT (US) 06516; Kevin R. Anderson, 15 Farm Brook Ct., Hamden, CT (US) 06514

(*) Notice: Subject to any disclaimer, the term of this patent is extended or adjusted under 35 U.S.C. 154(b) by 0 days.

(21) Appl. No.: 09/879,757

(22) Filed: Jun. 12, 2001

(65) Prior Publication Data
US 2002/0188246 A1 Dec. 12, 2002

(51) Int. Cl.[7] ............................................. A61M 5/00
(52) U.S. Cl. ...................... 604/8; 604/48; 604/500; 604/104; 604/264; 604/544
(58) Field of Search ............................ 604/104, 8, 48, 604/9, 10, 514, 517, 96.01, 264, 540, 544, 541, 93.01, 500

(56) References Cited

U.S. PATENT DOCUMENTS

| | | | |
|---|---|---|---|
| 4,155,364 A | | 5/1979 | Boxer |
| 4,248,214 A | | 2/1981 | Hannah et al. |
| 4,307,723 A | * | 12/1981 | Finney .................... 128/349 R |
| 4,531,933 A | * | 7/1985 | Norton et al. .................. 604/8 |
| 4,571,239 A | | 2/1986 | Heyman |
| 4,671,795 A | | 6/1987 | Mulchin |
| 4,787,884 A | * | 11/1988 | Goldberg ........................ 604/8 |
| 4,790,810 A | | 12/1988 | Pugh, Jr. et al. |
| 4,813,925 A | * | 3/1989 | Anderson, Jr. et al. ......... 604/8 |
| 4,911,163 A | | 3/1990 | Fina |
| 4,913,683 A | * | 4/1990 | Gregory ........................ 604/8 |
| 4,945,895 A | * | 8/1990 | Takai et al. .................... 1289/6 |
| 4,957,479 A | | 9/1990 | Roemer |
| 4,990,133 A | | 2/1991 | Solazzo |
| 5,007,898 A | | 4/1991 | Rosenbluth et al. |
| 5,019,102 A | * | 5/1991 | Hoene .......................... 632/12 |
| 5,116,309 A | * | 5/1992 | Coll .............................. 604/8 |
| 5,141,502 A | * | 8/1992 | Macaluso, Jr. .............. 604/281 |
| 5,221,253 A | | 6/1993 | Coll |
| 5,224,953 A | * | 7/1993 | Morgentaler ................. 606/192 |
| 5,282,784 A | * | 2/1994 | Willard .......................... 604/8 |
| 5,312,430 A | | 5/1994 | Rosenbluth et al. |
| 5,346,467 A | | 9/1994 | Coll |
| 5,354,263 A | | 10/1994 | Coll |
| 5,364,340 A | | 11/1994 | Coll |
| 5,380,270 A | * | 1/1995 | Ahmadzadeh ................. 604/9 |
| 5,470,307 A | | 11/1995 | Lindall |
| 5,554,147 A | | 9/1996 | Batich et al. |
| 5,599,291 A | * | 2/1997 | Balbierz et al. ................ 604/8 |
| 5,607,417 A | | 3/1997 | Batich et al. |
| 5,681,274 A | * | 10/1997 | Perkins et al. ................. 604/8 |
| 5,795,319 A | * | 8/1998 | Ali ................................ 604/8 |
| 5,954,652 A | * | 9/1999 | Heyman ...................... 600/435 |
| 6,066,113 A | * | 5/2000 | Overtoom .................... 604/96 |
| 6,280,434 B1 | * | 8/2001 | Kinoshita et al. ........... 604/530 |
| 6,364,868 B1 | * | 4/2002 | Ikeguchi ..................... 604/514 |

* cited by examiner

Primary Examiner—Ira S. Lazarus
Assistant Examiner—Tu Cam Nguyen
(74) Attorney, Agent, or Firm—DeLio & Peterson, LLC; Peter W. Peterson

(57) ABSTRACT

A method of treating the upper urinary tract of a mammal having a urethra extending to a bladder and a ureter extending from the bladder to a kidney. The method comprises initially extending a catheter system into the upper urinary tract, the catheter system having a urethral catheter infusion tube section extending through the urethra for infusion of a liquid; a urethral catheter drain tube section extending through the urethra for drainage of a liquid; a ureteral catheter tube section extending through a ureter into the kidney and having a first tube portion for infusion of a liquid connected to the urethral catheter infusion tube section, and a second tube portion for drainage of a liquid. The method then includes flowing a therapeutically effective liquid into the kidney through the urethral catheter infusion tube section and the ureteral catheter first, infusion tube portion, and, simultaneously with the flowing of the fluid into the kidney, draining fluid from the kidney through the urethral catheter drain tube section and the ureteral catheter second, drain tube portion.

30 Claims, 9 Drawing Sheets

COMBINATION URETERAL INFUSION CATHETER/DRAINAGE STENT

BACKGROUND OF THE INVENTION

1. Field of the Invention

The present invention relates generally to the field of ureteral stents and catheters. More particularly it relates to a ureteral catheter/stent combination that allows for continuous lavage of the upper urinary tract.

2. Description of the Prior Art

To date, medical therapy for pathologic conditions of the upper urinary tract has been less successful than treatment by surgical means. The relative resistance of the upper urinary tract to medical treatment is due both to the nature of the system itself and the nature of the common pathologic conditions that affect it. The upper urinary tract is, first of all, relatively inaccessible. In addition, the flow of urine from the kidney to the bladder cannot be impeded for any extended period of time without resultant kidney damage. Furthermore, medical management of pathologic conditions of this system, as, for example, chemolysis of kidney stones, may require prolonged application of agents. Nevertheless, finding a reliable and well-tolerated means of applying medicaments to the upper urinary tract is a worthwhile aim. Such a means could enhance the treatment of diseases affecting this system by providing a substitute for or a complement to the use of surgical techniques.

Various solutions have been attempted to meet the challenge of providing for medical treatment of conditions of the upper urinary tract. Prior art means that have been tried to achieve this goal have been found to have significant drawbacks. Oral medications such as potassium citrate have been used to treat conditions of the upper urinary tract by alkalinizing the urine in order to effect dissolution of uric acid kidney stones. Generally however, the effectiveness of oral medications is hampered because of dose limitation, the potential for systemic side effects, and patient non-compliance with regimens. Various stents and catheters are in common use, some using balloons, but they have been found by the applicants to have problems in delivery of medicaments to the renal pelvis and/or drainage of urine and other resulting fluids. Problems to date have included the inability of achieving an endurologic means of delivering adequate quantities of medication to the renal pelvis for periods of time sufficient to achieve the desired therapeutic result.

Bearing in mind the problems and deficiencies of the prior art, it is therefore an object of the present invention to provide an improved catheter system for delivering medicaments to the renal pelvis.

It is another object of the present invention to provide an improved medication-delivering catheter system that improves drainage from the renal pelvis.

A further object of the invention is to provide an endurologic means of delivering adequate quantities of medication to the renal pelvis.

It is yet another object of the present invention to provide a such an endurologic medication delivery means for periods of time sufficient to achieve the desired therapeutic result.

SUMMARY OF THE INVENTION

The above and other objects and advantages, which will be apparent to one of skill in the art, are achieved in the present invention which is directed to, in a first aspect, a urethral/ureteral catheter system comprising a urethral catheter infusion tube section adapted to extend through a urethra for infusion of a liquid and a urethral catheter drain tube section adapted to extend through a urethra for drainage of a liquid. There is also provided a ureteral catheter tube section adapted to extend through a ureter into a kidney and having a first tube portion for infusion of a liquid connected to the urethral catheter infusion tube section, and a second tube portion for drainage of a liquid. A curved, flexible tube portion at an end of the ureteral catheter section extends into the renal pelvis. The ureteral catheter tube section has a plurality of drain openings along a side wall thereof for receiving fluid to be drained from the kidney and a plurality of infusion openings along a side wall thereof for infusing fluid into the kidney.

Preferably, the ureteral catheter tube section drain openings extend a greater distance from the end of the ureteral catheter section than the ureteral catheter tube section infusion openings. The ureteral catheter tube section drain openings are also preferably further disposed on the ureteral catheter tube section adapted to extend through the ureter. The drain portion and the infusion portion of the ureteral catheter tube section may extend along side each other along at least a portion of the length thereof.

More preferably, at least some of the ureteral catheter tube section drain openings increase in size with increasing distance from the end of the ureteral catheter section, and at least some of the ureteral catheter tube section drain openings decrease in spacing with increasing distance from the end of the ureteral catheter section. The curved, flexible tube portion at an end of the ureteral catheter section may form a coil shape.

The ureteral catheter tube section first tube portion may have infusion openings only in the portion extending into the renal pelvis. Preferably, the ureteral catheter tube section second, drainage tube portion has a larger flow diameter than the ureteral catheter tube section first, infusion tube portion, and the end of the ureteral catheter section is tapered inward. At least some of the ureteral catheter tube section infusion openings may be closer to the end of the ureteral catheter section than the ureteral catheter tube section drain openings.

In a preferred embodiment, the ureteral catheter tube section second, drainage tube portion terminates at a lower end prior to the connection between the ureteral catheter tube section first, infusion tube portion and the urethral catheter infusion tube section. The ureteral catheter tube section second, drainage tube portion may have an opening at the lower end prior adapted to receive a guidewire for insertion along the length of the ureteral catheter tube section second, drainage tube portion.

In another aspect, the present invention is directed to a method of treating the upper urinary tract of a mammal having a urethra extending to a bladder and a ureter extending from the bladder to a kidney. The method comprises initially extending a catheter system into the upper urinary tract, the catheter system having a urethral catheter infusion tube section extending through the urethra for infusion of a liquid; a urethral catheter drain tube section extending through the urethra for drainage of a liquid; a ureteral catheter tube section extending through a ureter into the kidney and having a first tube portion for infusion of a liquid connected to the urethral catheter infusion tube section, and a second tube portion for drainage of a liquid. The method then includes flowing a fluid into the kidney through the urethral catheter infusion tube section and the ureteral catheter first, infusion tube portion, and, simultaneously with the flowing of the fluid into the kidney, draining fluid from the kidney through the urethral catheter drain tube section and the ureteral catheter second, drain tube portion. Preferably the infusion fluid comprises a therapeutically effective liquid for treating the kidney.

In practicing the method of the present invention, the ureteral catheter tube section has a drainage opening substantially sealed by walls of the uretero-pelvic junction prior to flowing the fluid into the kidney. After flowing the fluid into the kidney, these walls are dilated to expose the drainage opening at the uretero-pelvic junction.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF PREFERRED EMBODIMENTS

In describing the preferred embodiment of the present invention, reference will be made herein to FIGS. 1–13 of the drawings in which like numerals refer to like features of the invention. Features of the invention are not necessarily shown to scale in the drawings.

The present invention provides for the enhanced treatment of conditions of the upper urinary tract with an endurologic means of delivering adequate quantities of medication to the renal pelvis for periods of time sufficient to achieve the desired therapeutic result. The ureteral catheter/stent combination of the present invention does not impede the urinary drain, and provides an endurologic means of continuous and simultaneous infusion and drainage of a fluid from a point outside the body into and out of the upper urinary system. Such a prolonged, continuous lavage of the upper urinary tract is necessary if common pathologic conditions of this system, such as stones and tumors, are to be treated medically.

The catheter/stent combination of the present invention is divided for the convenience of explanation into two main sections: i) the ureteral portion or section, also referred to as the ureteral catheter/stent, and ii) the bladder drainage portion, also referred to as the Foley catheter or urethral catheter section. The end of the ureteral catheter/stent that rests in the renal pelvis will be referred to as the kidney or proximal end.

The catheter/stent combination of the present invention is made of a biocompatible material such as a polyurethane, for example Percuflex (sold by Microvasive, Boston Scientific Corp.), having the proximal, i.e., kidney, end preformed into a coil or other shape sufficient to prevent migration. The longitudinal axis of the stent includes two lumens or interior channels, one for fluid infusion into the kidney and one for continuous fluid drainage from the kidney. The ureteral catheter section infusion lumen preferably has side perforations along only its proximal aspect corresponding to the segment of the device that sits in the renal pelvis. When in position in the body, this lumen then extends from the renal pelvis along the length of the ureter. In the preferred embodiment it is connected in the bladder to a bladder drainage catheter where it continues as a separate lumen. The lumen ends in a side port on a portion of the bladder drainage catheter external to the body. It thus provides a means for infusing fluid into the kidney.

The ureteral stent portion extends from the renal pelvis to the bladder. It is equipped with drainage side ports along its entire ureteric length. The size, shape and/or density of the side ports are increased at the segment of the stent that, when implanted, abuts the ureteropelvic junction. This arrangement of side ports allows for the renal collecting system to become physiologically distended during the lavage process. This effect is important because it ensures that the entire collecting system surface of the kidney is exposed to the therapeutic agent being instilled.

Upon initiation of infusion the paucity of side ports on the intra-renal portion of the stent assures sluggish drainage of the system. Thus, at this stage, the rate of inflow exceeds the rate of outflow, the collecting system of the kidney fills with fluid and the normally collapsed calices become dilated. The dilatation of the collecting system also distends the ureteropelvic junction. This distension exposes the drainage side ports located at segment of the stent abutting this area. With exposure of these drainage means, efficient drainage of the system ensues and further distension is prevented before abnormal intra-renal pressures are reached. A steady state is achieved wherein the therapeutic agent is being continuously infused into and drained from the renal cavity while at the same time the cavity is physiologically distended. Thus, the apparatus and method disclosed allows for efficient, continuous, endourologic infusion and drainage of liquid agents and medicaments into and out of the upper urinary tract on a long term basis in a manner that allows for the entire upper tract urothelial surface to be bathed in the therapeutic fluid.

Figure 1:
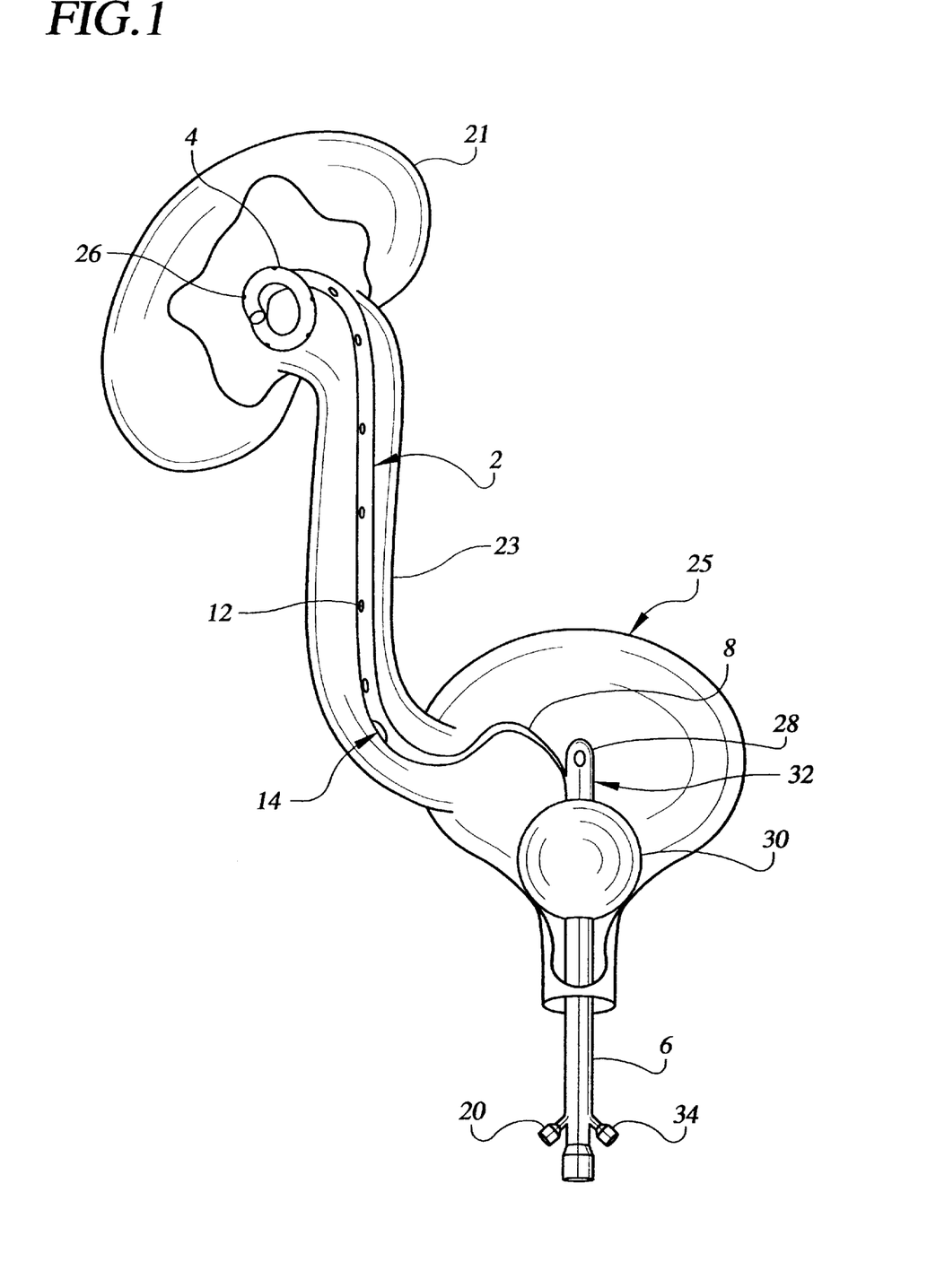
FIG. 1 is an elevational view of a preferred embodiment of the ureteral catheter/stent combination of the present invention after it has been placed into the urinary tract.

A preferred embodiment of the catheter/stent combination of the present invention is depicted in FIGS. 1–13. As shown in FIG. 1, the ureteral catheter/stent 2 has a flexible, elongated, hollow tubular structure. The proximal end forms a pigtail or coil 4 in the renal pelvis 21 by which it maintains its position after placement. The ureteral catheter/stent extends from the renal pelvis 21 along the length of the ureter 23 and into the bladder 25. The ureteral catheter portion extends beyond the ureteral stent portion and is integrated into the Foley catheter 32 in bladder 25 and urethra 27.

Figure 2:
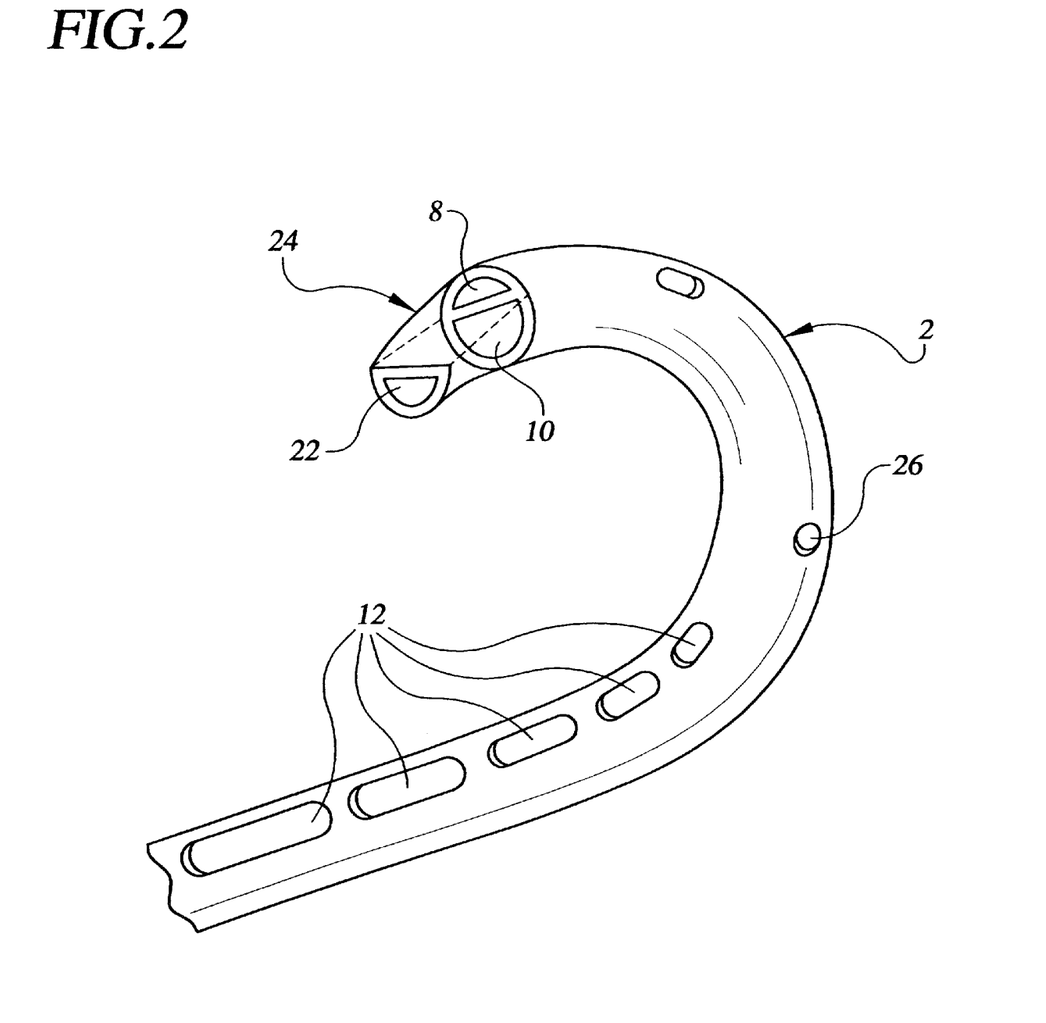
FIG. 2 is a perspective view, partially in section, of the proximal or kidney end of the ureteral catheter/stent combination shown in FIG. 1.
Figure 3:
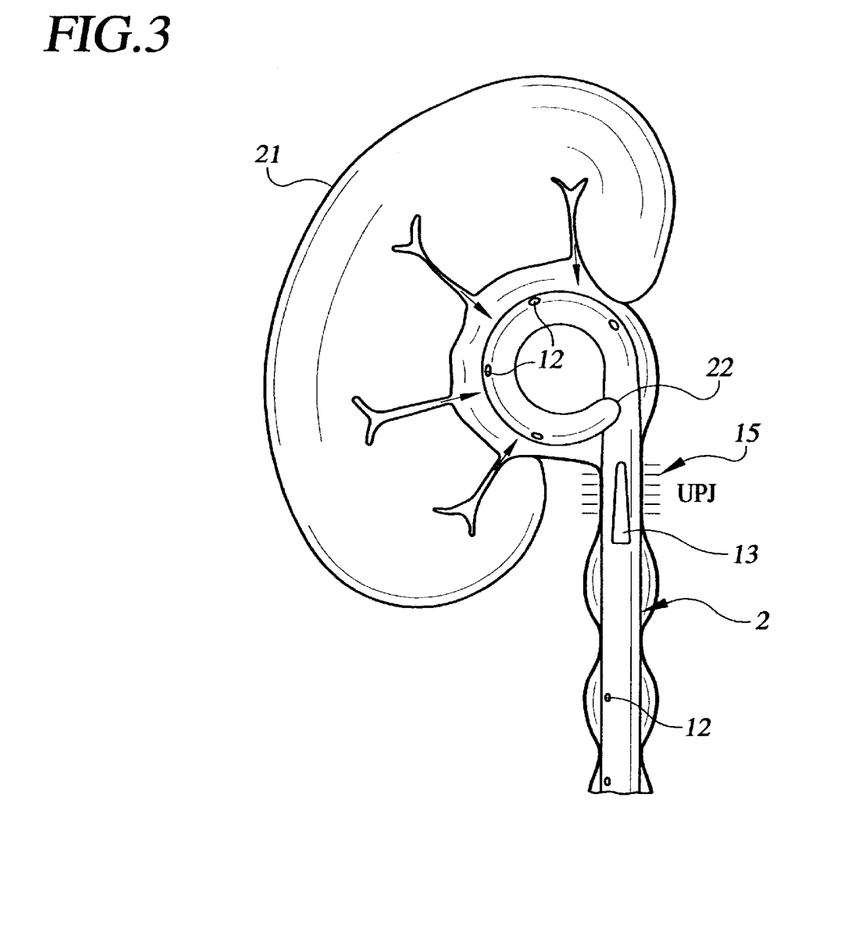
FIG. 3 is an elevational view of an alternate embodiment of the present invention installed in the urinary tract with the renal pelvis decompressed, before infusion.

FIG. 2 depicts the kidney end of the ureteral stent/catheter, which terminates in an end opening 22 continuous with the drain tube section or lumen 10 extending through the length of the ureteral stent portion of the device. Drain tube section or lumen 10 communicates with drainage side ports 12. Preferably, the distance between such openings decreases, and the size of the openings increase, with increasing distance from end 22. This is shown in FIG. 2 where the major diameters (along the length of the tube) of openings 12 increase, and the spacing between openings 12 decrease, with increasing distance from end 22. Instead of the circular or oval openings shown, the openings may be of other shape, such as triangular, as shown in FIG. 3. Ureteral catheter/stent 2 is installed in the urinary tract, with the renal pelvis decompressed, before infusion, and a drainage triangular opening 13 is disposed at the uretero-pelvic junction (UPJ) 15. Triangular opening 13 is oriented so that the smallest width across the tube is closest to end 22, and the opening increases in width or size with increasing distance from end 22. It should be noted that, before infusion takes place with the present invention, the calices and renal pelvis 21 are decompressed and the drainage opening at UPJ 15 is substantially sealed by the junction walls. At this time, urine produced by the kidney is drained primarily through the opening in end 22.

Also shown in FIG. 2 is infusion tube section or lumen 8 of the ureteral catheter portion which extends within the ureteral stent/catheter alongside drain tube section 10, and is preferably of smaller cross-section than drain tube 10. The infusion tube section or lumen 8 extends through the length of the ureteral catheter portion of the device and tapers inwardly to a closed, blind end 24 adjacent stent portion end opening 22. Preferably, the infusion tube section or lumen 8 of the ureteral catheter portion of the device has infusion portholes or openings 26 only along its kidney end. The infusion portholes or openings 26 extend closer to end 22 than do drainage ports 12.

Figure 4:
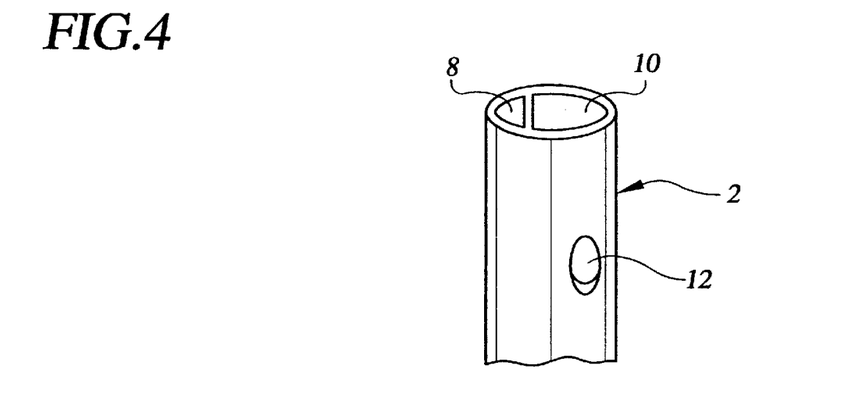
FIG. 4 shows a cross-sectional cut of a mid-ureteral portion of the ureteral catheter/stent combination shown in FIG. 1.

A cut through the mid-ureteral portion of the ureteral catheter/stent 2 is depicted in FIG. 4 showing how it is divided into lumens, 8 and 10, of different diameters. The ureteral stent/catheter is divided into these two separate lumens from its kidney end to a position down the ureter or into the bladder. Ureteral drain tube section 10 continues to have a larger flow diameter than ureteral infusion tube section 8. Drainage holes 12 formed through the outer wall are located at various points along the ureteric length of the ureteral stent portion of the device, and facilitate drainage of fluids from the collecting system to the bladder.

Figure 5:
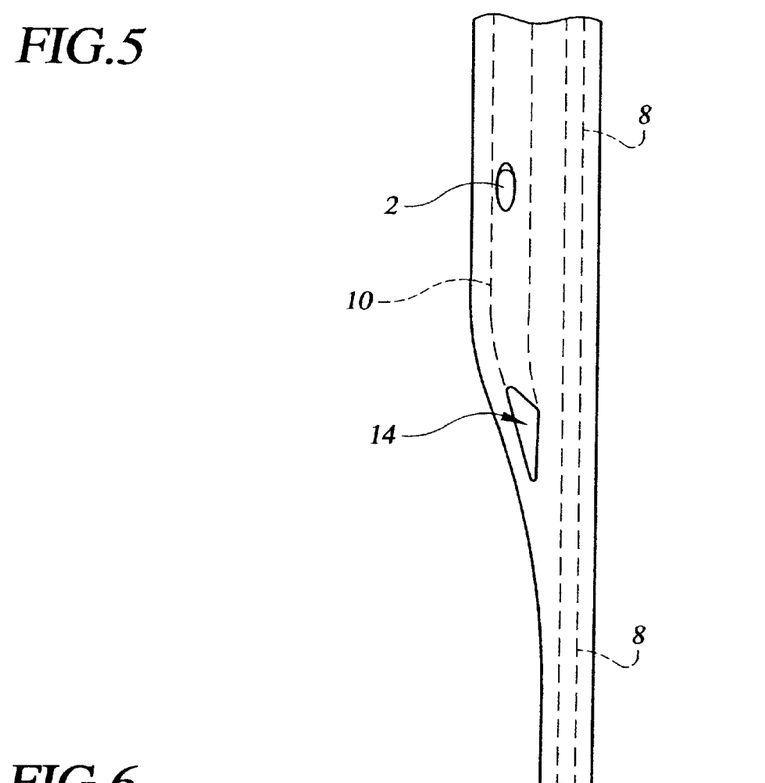
FIG. 5 is an elevational view of the terminal end of the ureteral stent portion of the ureteral catheter/stent combination shown in FIG. 1 showing the interior channels in phantom lines.
Figure 6:
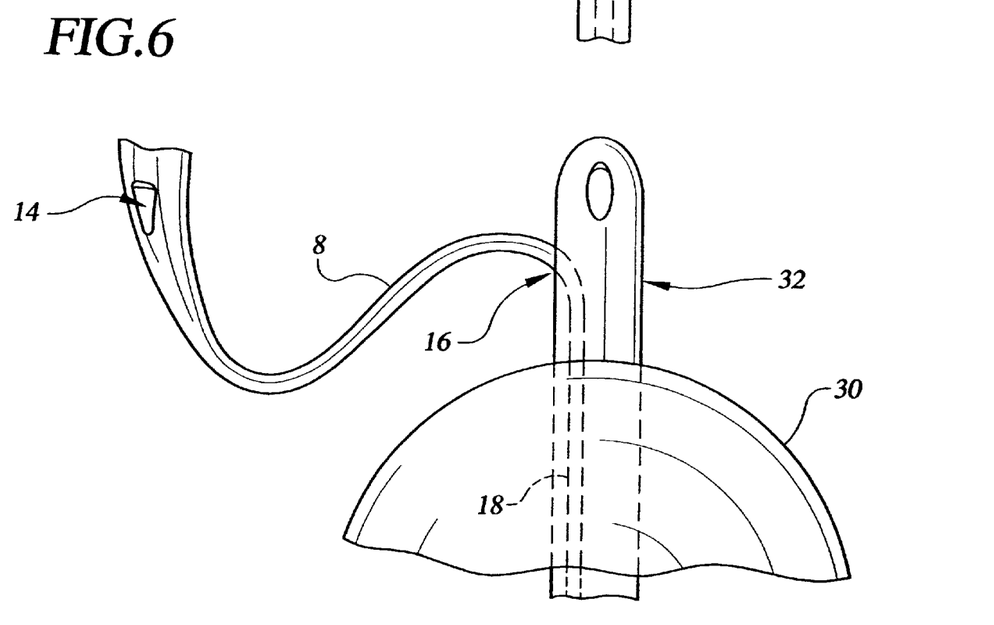
FIG. 6 is a perspective view of the ureteral catheter/stent combination of FIG. 1 showing the integration of the ureteral catheter portion of the invention into the bladder drainage catheter.
Figure 7:
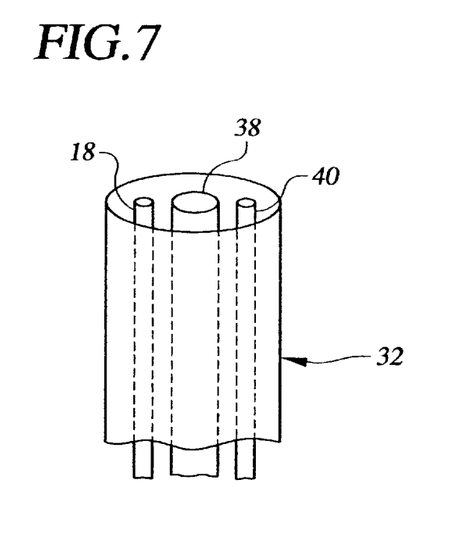
FIG. 7 shows a cross-sectional cut of the Foley catheter tube portion of the ureteral catheter/stent combination of FIG. 1 showing the three interior channels in phantom lines.
Figure 8:
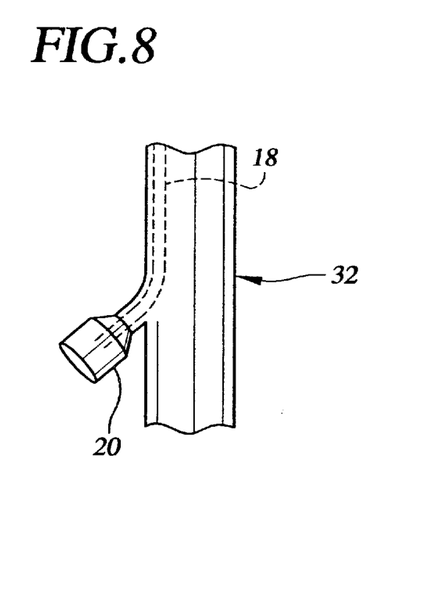
FIG. 8 is an elevational view of the ureteral catheter/stent combination of FIG. 1 showing the access port and interior channel (in phantom lines) located near the distal end of the bladder drainage catheter.
Figure 9:
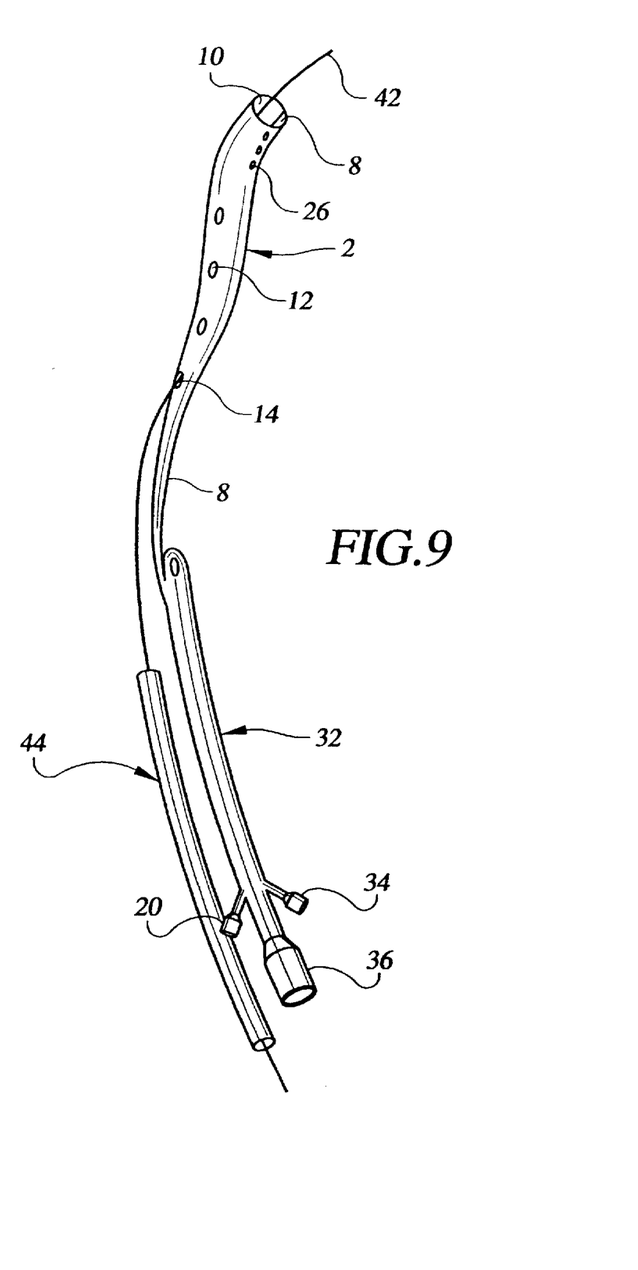
FIG. 9 is an elevational view depicting the ureteral catheter/stent combination shown in FIG. 1 being placed over a guide wire.

As shown in FIG. 5, drain lumen 10 of the ureteral stent portion of the device is tapered at its distal end, which terminates in an open-end drainage port 14. This drainage port is of a sufficient size or caliber to allow for the admittance of a standard guidewire. The infusion tube or lumen 8 of the ureteral catheter portion continues on, in a direction away from the kidney end, beyond the point where the drain lumen 10 terminates. The ureteral catheter portion and infusion tube 8 extends as far as, and is connected to, the infusion tube of the otherwise standard Foley catheter 32 (FIG. 6). After the point of connection 16, the infusion is made via a separate infusion lumen 18 within the Foley catheter. FIG. 7 shows a cross-section of the shaft of the Foley catheter 32 which contains infusion lumen 18, bladder drainage lumen 38, and balloon inflation lumen 40. In FIG. 8 the infusion lumen terminates in an access port 20 near the distal end of the Foley catheter 32.

In use, the ureteral catheter infusion portion of the device extends as a continuous tube from the kidney 21 end of the device to a port along the length of the Foley catheter external to the body (FIG. 1). Portholes 26, along the kidney end of the ureteral catheter portion of the device, allow for liquid agents instilled through the access port 20 to be dispersed into the collecting system of the kidney 21.

Figure 10:
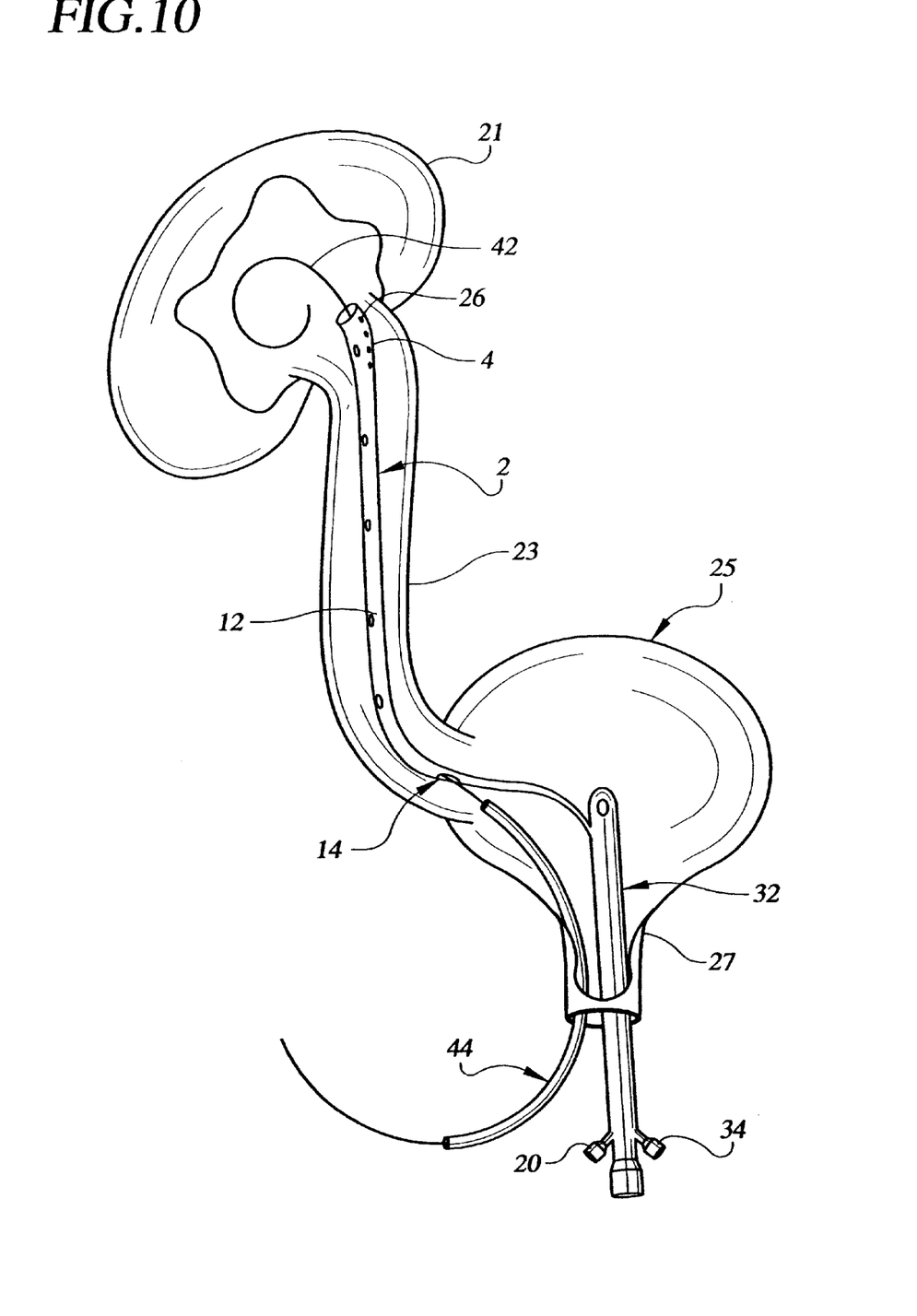
FIG. 10 is an elevational view depicting the ureteral catheter/stent combination shown in FIG. 1 being advanced into position over the guide wire with the aid of a stent pusher.

Placement of the assembly would begin in a manner similar to the placement of a conventional stent. The physician passes a guidewire up to the kidney 21. As FIG. 9 demonstrates, the ureteral stent portion of the ureteral segment of the assembly 10, is fed co-axially over the guide wire 42. The ureteral catheter portion 8 and the Foley catheter 32 are not intubated by the guide wire, 42. A stent pusher 44, also fed co-axially over the guidewire, may be advanced until the proximal tip contacts the terminal end of the ureteral stent end opening 14. FIG. 10 illustrates how, under fluoroscopic control, the device is advanced with the stent pusher 44 through urethra 27, bladder 25 and ureter 23 so that the kidney end of the assembly is positioned within the renal pelvis 21. As this is happening, the bladder drainage catheter 32 is drawn into the urethra 27. With manual assistance, the Foley catheter 32 is advanced into the bladder 25 simultaneous to the advancement of the stent pusher, 44. Once the coil 4 at the kidney 21 end of the device has been positioned properly, the Foley catheter 32 may be advanced independent of the stent pusher 44.

Figure 11:
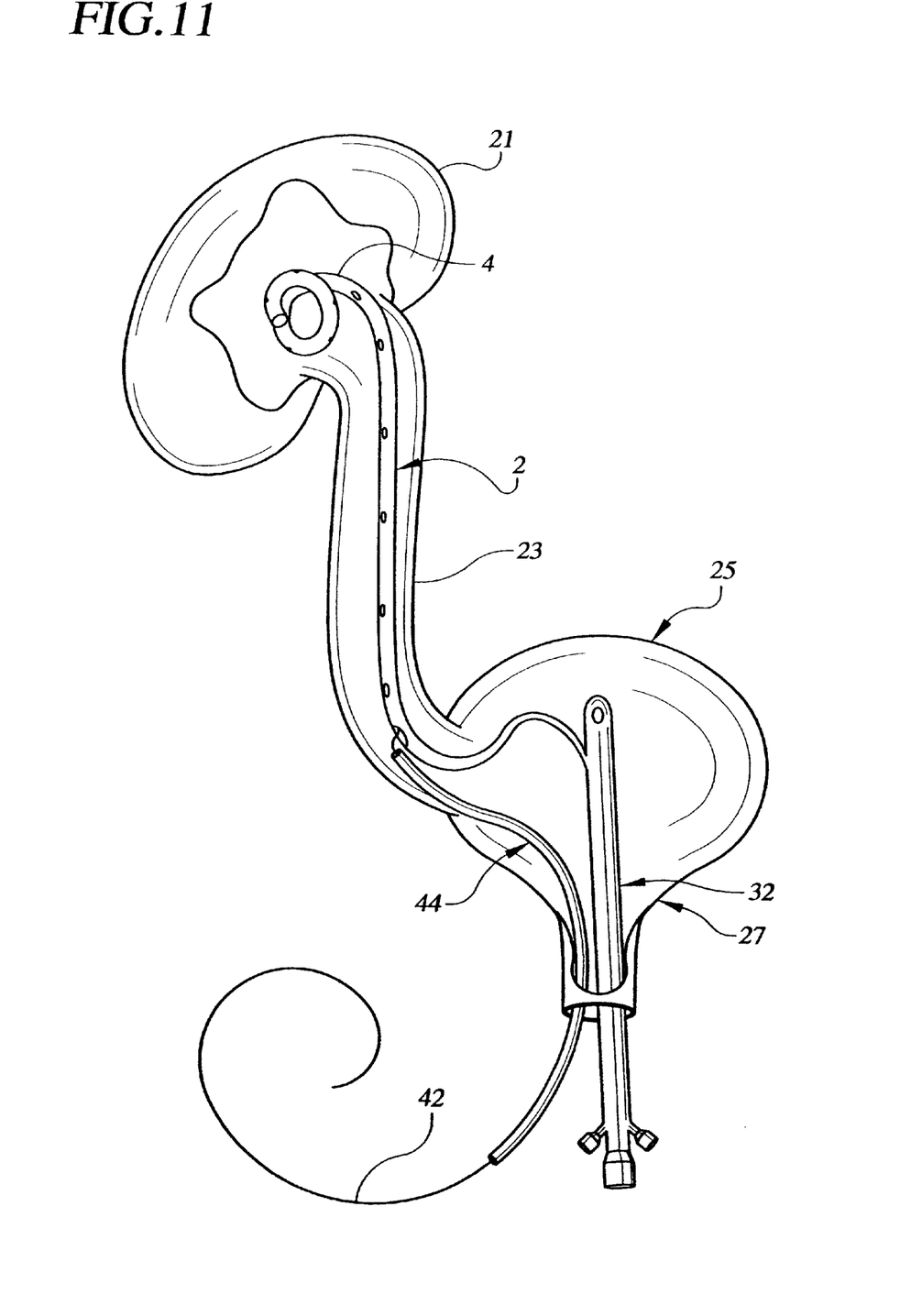
FIG. 11 is an elevational view depicting the ureteral catheter/stent combination shown in FIG. 1 in position in the kidney with the guide wire being removed.
Figure 12:
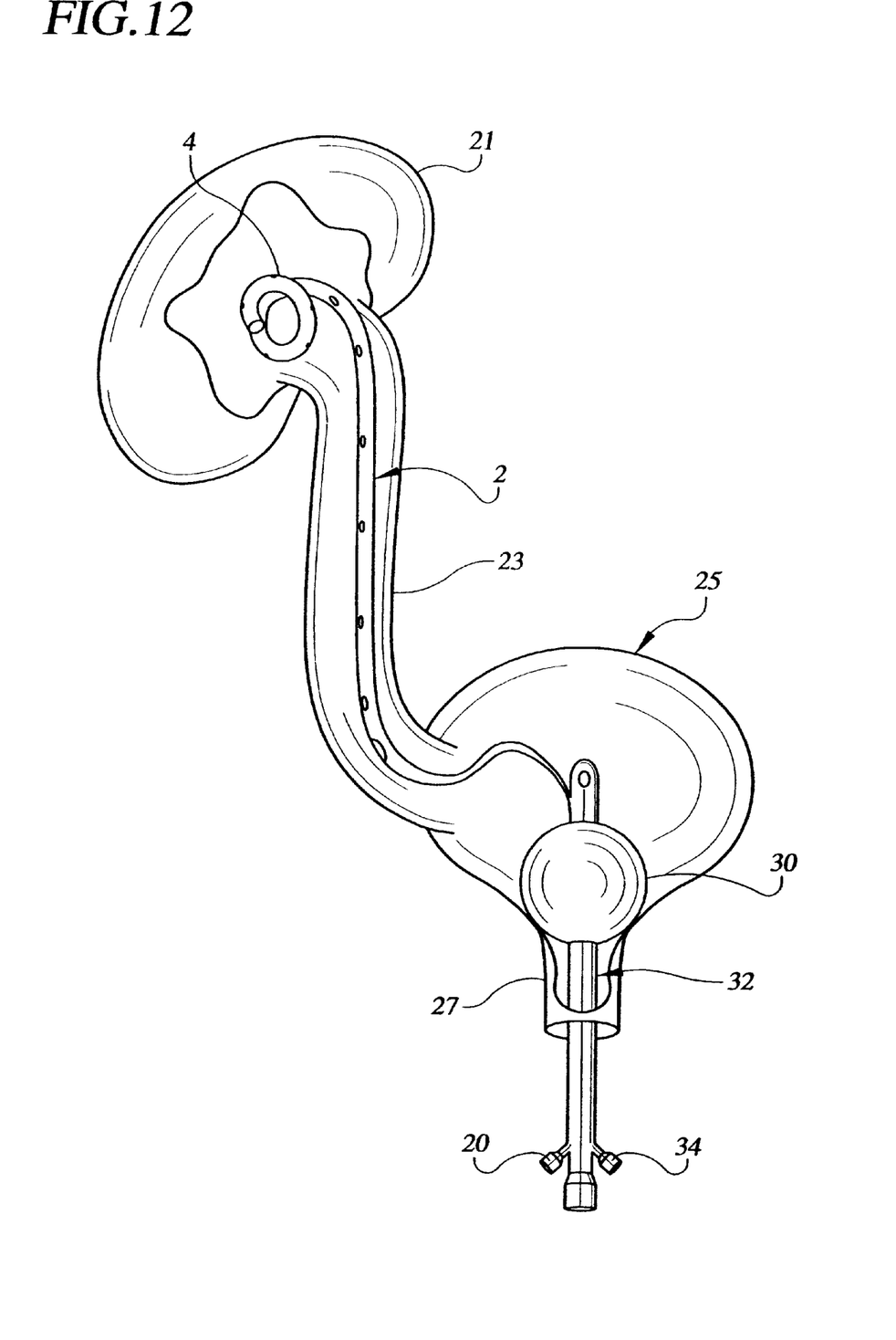
FIG. 12 is an elevational view depicting the ureteral catheter/stent combination shown in FIG. 1 after installation in the kidney with the Foley catheter balloon inflated.

As illustrated in FIG. 11, when the Foley catheter has entered the bladder, the position of the ureteral portion of the device can be maintained with the stent pusher 44 as the guide wire 42 is removed. The kidney coil 4 forms at the kidney end to permit retention of the ureteral portion within the kidney 21. Once the guide wire 42 has been removed, the pusher 44 can be removed, and the Foley catheter balloon 30 can be inflated, as shown in FIG. 12. The proper position of the stent can be confirmed fluoroscopically. Efflux of urine through the Foley catheter 32 will confirm its proper placement. With the assembly thus installed, access to the renal pelvis is available through the infusion side port 20 on the shaft of the Foley catheter external to the body. As indicated, fluid agents and medicaments may be infused through this port to aid in the treatment of pathologic conditions of the upper urinary tract.

Figure 13:
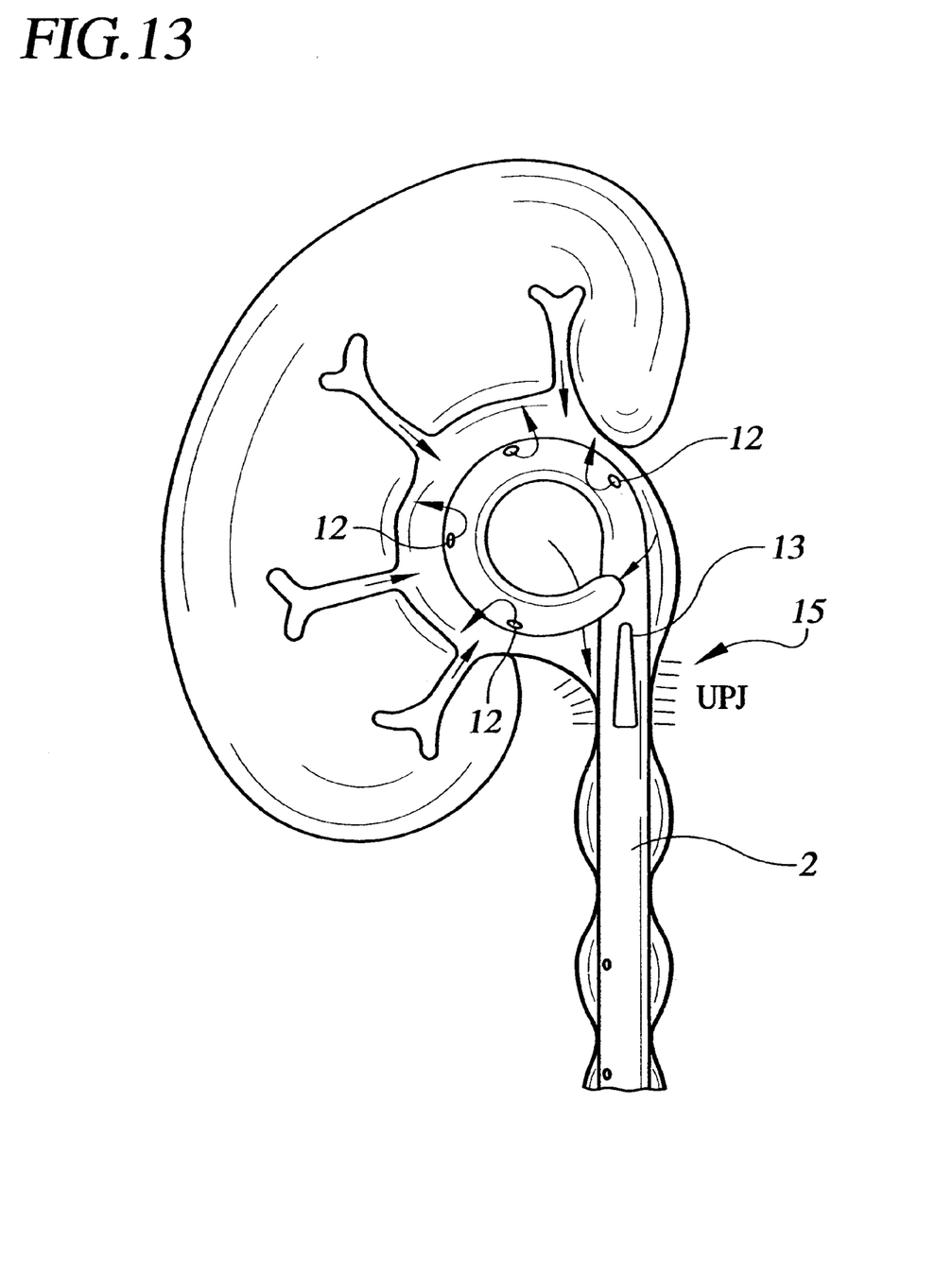
FIG. 13 is an elevational view of an alternate embodiment of the present invention installed in the urinary tract with the renal pelvis dilated, with active infusion.

FIG. 13 shows the ureteral catheter/stent 2 after installation in the kidney with active infusion occurring. The calices and renal pelvis 21 are dilated, so that the drainage opening 13 at the UPJ 15 is exposed. Infusate and urine produced by the kidney is drained through the end opening 22, as well as the side drainage openings 12 and 13.

The present invention provides a particularly effective lavage method of treating the upper urinary tract of humans and other mammals. After extending the catheter system into the upper urinary tract as described above, fluid agents and medicaments may be continuously or discontinuously flowed into the kidney through the urethral catheter infusion tube section and the ureteral catheter first, infusion tube portion. Simultaneously with the flowing of the fluid into the kidney, the method provides for continuously draining fluid from the kidney through the urethral catheter drain tube section and the ureteral catheter second, drain tube portion. The structural features of the present invention provide for such concurrent, steady state infusion and draining of fluids to and from the kidney, particularly in the preferred embodiment where the cross-section of the ureteral catheter drainage tube portion is greater and has a larger flow diameter than that of the ureteral catheter infusion tube portion. In this preferred embodiment, the relative larger flow diameter of the drainage tube should continue through the urethral section also so as to prevent flow constriction.

Following the desired treatment, removal of the device is achieved by first deflating the balloon of the Foley catheter 30. Gentle traction is then applied to the distal end of the Foley catheter, 32, in order to progressively and completely withdraw the device from the urinary tract.

It will be apparent that other embodiments may exist that meet some or all of the objectives set forth in this disclosure. For example, the double lumen ureteral catheter/stent could be replaced by a single lumen ureteral stent that would also be integrated into a bladder drainage catheter. Such an iteration would provide for greater comfort and ease of removal of a stent used in a standard fashion. Or, for instance, a double lumen ureteral catheter/stent that could be accessed at cystoscopically at intervals for the purpose of infusing agents and medicaments into the renal pelvis is easily conceived of and could stand as an embodiment of this invention. Furthermore, a double lumen ureteral stent in which the ureteral catheter portion extend distal to the ureteral stent portion and exited the urethra can also easily be envisioned. It is the intent of the appended claims to cover all such variations and modifications that come within the spirit and scope of this invention.

Thus, the present invention achieves the objects stated above. The dual lumen combination urethral/ureteral catheter system provides an indwelling, endourologic means and method of continuous lavage of the upper urinary tract from a point outside the body.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A urethral/ureteral catheter system comprising:
   a urethral catheter infusion tube section adapted to extend through a urethra for infusion of a liquid;
   a urethral catheter drain tube section adapted to extend through a urethra for drainage of a liquid;
   a ureteral catheter tube section adapted to extend through a ureter into a kidney and having a first tube portion for infusion of a liquid connected to the urethral catheter infusion tube section, and a second tube portion for drainage of a liquid; and
   a curved, flexible tube portion at an end of the ureteral catheter section adapted to extend into the renal pelvis, the ureteral catheter tube section having a plurality of drain openings along a side wall thereof for receiving fluid to be drained from the kidney and a plurality of infusion openings along a side wall thereof for infusing fluid into the kidney.

2. The catheter system of claim 1 wherein the ureteral catheter tube section drain openings extend a greater distance from the end of the ureteral catheter section than the ureteral catheter tube section infusion openings.

3. The catheter system of claim 1 wherein the ureteral catheter tube section drain openings are further disposed on the ureteral catheter tube section adapted to extend through the ureter.

4. The catheter system of claim 1 wherein the drain portion and the infusion portion of the ureteral catheter tube section extend along side each other along at least a portion of the length thereof.

5. The catheter system of claim 1 wherein at least some of the ureteral catheter tube section drain openings increase in size with increasing distance from the end of the ureteral catheter section.

6. The catheter system of claim 1 wherein at least some of the ureteral catheter tube section drain openings decrease in spacing with increasing distance from the end of the ureteral catheter section.

7. The catheter system of claim 1 wherein the curved, flexible tube portion at an end of the ureteral catheter section forms a coil shape.

8. The catheter system of claim 1 wherein the ureteral catheter tube section first tube portion has infusion openings only in the portion extending into the renal pelvis.

9. The catheter system of claim 1 wherein the ureteral catheter tube section second, drainage tube portion has a larger flow diameter than the ureteral catheter tube section first, infusion tube portion.

10. The catheter system of claim 1 wherein the end of the ureteral catheter section is tapered inward.

11. The catheter system of claim 1 wherein at least some of the ureteral catheter tube section infusion openings are closer to the end of the ureteral catheter section than the ureteral catheter tube section drain openings.

12. The catheter system of claim 1 wherein the ureteral catheter tube section second, drainage tube portion terminates at a lower end prior to the connection between the ureteral catheter tube section first, infusion tube portion and the urethral catheter infusion tube section.

13. The catheter system of claim 12 wherein the ureteral catheter tube section second, drainage tube portion has an opening at the lower end prior adapted to receive a guidewire for insertion along the length of the ureteral catheter tube section second, drainage tube portion.

14. A method of treating the upper urinary tract of a mammal having a urethra extending to a bladder and a ureter extending from the bladder to a kidney comprising:
   extending a catheter system into the upper urinary tract, the catheter system having a urethral catheter infusion tube section extending through the urethra for infusion of a liquid; a urethral catheter drain tube section extending through the urethra for drainage of a liquid; a ureteral catheter tube section extending through a ureter into the kidney and having a first tube portion for infusion of a liquid connected to the urethral catheter infusion tube section, and a second tube portion for drainage of a liquid;

flowing a fluid into the kidney through the urethral catheter infusion tube section and the ureteral catheter first, infusion tube portion; and simultaneously with the flowing of the fluid into the kidney, draining fluid from the kidney through the urethral catheter drain tube section and the ureteral catheter second, drain tube portion.

15. The method of claim 14 wherein the ureteral catheter tube section has a drainage opening substantially sealed by walls of the uretero-pelvic junction prior to flowing the fluid into the kidney, and wherein after flowing the fluid into the kidney said walls are dilated to expose the drainage opening at the uretero-pelvic junction.

16. The method of claim 14 wherein the infusion fluid comprises a therapeutically effective liquid for treating the kidney.

17. The method of claim 14 wherein the catheter system includes a curved, flexible tube portion at an end of the ureteral catheter section adapted to extend into the kidney.

18. The method of claim 14 wherein the ureteral catheter tube section has a plurality of drain openings along a side wall thereof for receiving fluid to be drained from the kidney and a plurality of infusion openings along a side wall thereof for infusing fluid into the kidney.

19. The method of claim 14 wherein the ureteral catheter tube section drain openings extend a greater distance from the end of the ureteral catheter section than the ureteral catheter tube section infusion openings.

20. The method of claim 14 wherein the ureteral catheter tube section drain openings are further disposed on the ureteral catheter tube section adapted to extend through the ureter.

21. The method of claim 14 wherein the drain portion and the infusion portion of the ureteral catheter tube section extend along side each other along at least a portion of the length thereof.

22. The method of claim 14 wherein at least some of the ureteral catheter tube section drain openings increase in size with increasing distance from the end of the ureteral catheter section.

23. The method of claim 14 wherein at least some of the ureteral catheter tube section drain openings decrease in spacing with increasing distance from the end of the ureteral catheter section.

24. The method of claim 14 wherein the curved, flexible tube portion at an end of the ureteral catheter section forms a coil shape.

25. The method of claim 14 wherein the ureteral catheter tube section first tube portion has infusion openings only in the portion extending into the kidney.

26. The method of claim 14 wherein the ureteral catheter tube section second, drainage tube portion has a larger flow diameter than the ureteral catheter tube section first, infusion tube portion.

27. The method of claim 14 wherein the end of the ureteral catheter section is tapered inward.

28. The method of claim 14 wherein at least some of the ureteral catheter tube section infusion openings are closer to the end of the ureteral catheter section than the ureteral catheter tube section drain openings.

29. The method of claim 14 wherein the ureteral catheter tube section second, drainage tube portion terminates at a lower end prior to the connection between the ureteral catheter tube section first, infusion tube portion and the urethral catheter infusion tube section.

30. The catheter system of claim 28 wherein the ureteral catheter tube section second, drainage tube portion has an opening at the lower end prior adapted to receive a guidewire for insertion along the length of the ureteral catheter tube section second, drainage tube portion.

* * * * *